(12) United States Patent
Echols et al.

(10) Patent No.: US 7,758,883 B2
(45) Date of Patent: Jul. 20, 2010

(54) THREE LAYER ARTIFICIAL TEAR FORMULATION

(75) Inventors: Joel S. Echols, Birmingham, AL (US); Frank J. Holly, Yantis, TX (US); Wolfgang Widera, Lagenfeld (DE)

(73) Assignee: Aqueous Pharma Limited, Lisbon (PT)

( * ) Notice: Subject to any disclaimer, the term of this patent is extended or adjusted under 35 U.S.C. 154(b) by 1879 days.

(21) Appl. No.: 10/688,539

(22) Filed: Oct. 17, 2003

(65) Prior Publication Data

US 2004/0142038 A1  Jul. 22, 2004

Related U.S. Application Data

(60) Provisional application No. 60/419,428, filed on Oct. 18, 2002.

(51) Int. Cl.
*A61F 2/00* (2006.01)
*A61K 9/107* (2006.01)

(52) U.S. Cl. .................................... 424/427; 424/428

(58) Field of Classification Search ................ 424/427, 424/428
See application file for complete search history.

(56) References Cited

U.S. PATENT DOCUMENTS

| | | | |
|---|---|---|---|
| 2,897,120 A * | 7/1959 | Cronin et al. ............... | 424/489 |
| 4,421,748 A | 12/1983 | Trager et al. | |
| 4,744,980 A | 5/1988 | Holly | |
| 4,818,537 A | 4/1989 | Guo | |
| 4,883,658 A * | 11/1989 | Holly ...................... | 514/772.3 |
| 4,914,088 A | 4/1990 | Glonek et al. | |
| 5,221,696 A | 6/1993 | Ke et al. | |
| 5,290,572 A | 3/1994 | MacKeen | |
| 5,371,108 A | 12/1994 | Korb et al. | |
| 5,540,930 A * | 7/1996 | Guy et al. ................... | 424/427 |
| 5,800,807 A | 9/1998 | Hu et al. | |
| 6,132,751 A * | 10/2000 | Suzuki et al. ............... | 424/422 |
| 6,429,227 B1 | 8/2002 | Schneider et al. | |
| 6,565,861 B1 | 5/2003 | Tiffany et al. | |

FOREIGN PATENT DOCUMENTS

| | | |
|---|---|---|
| EP | 0 448 762 A1 | 10/1991 |
| EP | 1 020 194 A1 | 7/2000 |
| WO | WO 83/00091 | 1/1983 |

\* cited by examiner

*Primary Examiner*—Gollamudi S Kishore
(74) *Attorney, Agent, or Firm*—Preti Flaherty Beliveau & Pachios LLP

(57) ABSTRACT

An artificial tear film over the surface of an eye having a first layer in direct contact with the ocular surface, an aqueous layer over the first layer, and a layer of a phospholipid over the aqueous layer. The first layer has polyvinyl alcohol, polyvinyl acetate, and polyvinyl pyrrolidone. The phospholipid is derived from Amisol® Clear. The artificial tear film is effective in significantly prolonging the tear break up time in patients with dry eye syndrome.

4 Claims, No Drawings

THREE LAYER ARTIFICIAL TEAR FORMULATION

This non-provisional patent application claims the benefit of the related provisional patent application, Ser. No. 60/419,428, filed on Oct. 18, 2002, which is incorporated herein by reference.

FIELD OF THE INVENTION

The present invention relates generally to the field of artificial tear formulations for the treatment of dry eye syndrome and protection of the ocular surface. More specifically, the present invention relates to artificial tear formulations having polyvinyl alcohol, polyvinyl acetate, a hydrophilic polymer, and a phospholipid for replicating all three layers of the normal human tear film.

BACKGROUND OF THE INVENTION

The human tear provides a protective film that covers the ocular surface, thereby preventing ocular discomfort and damage to the ocular surface. A healthy human tear film consists of a delicate balance of three layers, namely, the outermost lipid layer, the innermost mucin layer adjacent to the ocular surface, and the middle aqueous layer. The lipid layer, the outermost layer of the tear film, seals the tear film to prevent evaporation and maintain the structural integrity of the tear film. The lipid layer is produced by the meibomian glands found in the eyelids. The aqueous layer, the middle layer of the tear film, functions to cleanse the eye and deliver oxygen to the avascular cornea, and to provide other nutrients and protectants to the eye, including immune-system proteins that help prevent microbial or toxic substances from reaching the ocular surface. The aqueous (watery) layer is produced primarily by the lacrimal glands. The mucin layer, which is the innermost layer adjacent the ocular surface, is produced by the goblet cells of the conjunctiva and cornea. The mucin layer serves to coat the hydrophobic corneal epithelium with a hydrophilic layer. The mucin layer helps the aqueous layer spread over the ocular surface and allows the surface to become hydrophilic. The mucin layer contributes to maintaining hydration of the ocular surface and preventing pathogens from reaching the ocular surface.

The three layered tear film is critical in maintaining the integrity of the tear film, which, in turn, maintains the integrity of the ocular surface. A compromised tear film can cause drying of the ocular surface. The condition of dry eye syndrome, medically known as keratoconjunctivitis sicca (KCS), is the term for a number of clinical disease states characterized by disturbances in the pre-ocular tear film resulting in ocular surface disease. KCS accounts for the highest percentage of patient visits to ophthalmologists, and its treatment has given rise to a global pharmaceutical market of over 3 billion dollars.

Dry eye syndrome can originate from a variety of causes. In the report of the National Eye Institute/Industry Workshop on Clinical Trials in Dry Eyes issued in 1995, a new classification system for the various types of dry eye syndrome was presented. The two major categories are:

I. Evaporative Type

One cause of this type is meibomian gland dysfunction, which leads to a deficiency and/or alteration in the lipid layer of the tear film, and the resulting premature evaporation of the tear film. Contact lens wear also contributes to evaporative KCS and this is a double-edge sword, as a lipid deficient dry eye will also act to prevent many people from comfortably wearing of contact lenses. Blinking abnormality also leads to evaporative KCS. The mucin layer also plays a major role in this classification, as the mucus must provide wettability directly on the epithelial cells of the cornea and conjunctiva, which is greatly improved by a higher oncotic pressure, optimally greater than 45 mmHg.

II. Aqueous Tear Production Deficient Type

There are two primary subcategories of the aqueous tear production deficient type. The first subcategory, Non-Sjögren's Associated KCS, is by far the most common. It is caused by a decrease in lacrimal glands secretions due to numerous factors, including but not limited to old age, and the use of certain medications such as oral antihistamines and antidepressants, which can cause ocular dryings as a side effect. The second subcategory, Sjögren's Associated KCS, is related to the autoimmune disease Sjögren's Syndrome, which involves the body's immune system turning against the host. As related to KCS, Sjögren's Syndrome causes permanent damage to the lacrimal glands, resulting in a deficiency in tear production. Patients with Sjögren's Syndrome also experience dry mouth, dry skin, vaginal dryness and, in 20% of the cases, rheumatoid arthritis.

Each time a person blinks the tear film is reformed and, therefore, remains intact. A primary goal of treating KCS is to achieve an extension in the time the tear film remains intact after a blink. As the eye remains open after a blink, at some duration of time as the eye remains open, the tear film will breakup and the ocular surface will become exposed and unprotected until the next blink. It can be appreciated that even minute differences in the duration of tear film integrity can make a difference in the clinical profile of a KCS patient, because the repeated intermittent exposures can lead to ocular surface damage. Thus, a primary goal of dry-eye therapies is to achieve an extension in the time the tear film remains intact.

A mainstay in the treatment of KCS is the use of artificial tear formulations. Currently, approximately 35 million people, worldwide require the use of artificial tear formulations. An ideal artificial tear formulation would be able to achieve a lengthening of tear film breakup time while also being comfortable in the eye. A tear substitute needs to provide sufficient reduction of tear film breakup to bridge the gap between the tear film breakup time and time between blinks, in order to provide improved ocular surface protection. At the same time, the tear substitute also needs to be comfortable in the eye.

Commercially available artificial tear formulations do not adequately replicate all three layers of the normal human tear film. Numerous research supports the importance of the lipid layer, with one of the most significant studies by Drs. Heiligenhaus, Koch, Kruse, Schwarz and Waubke at the University of Essen Eye Clinic (Germany), in which 110 dry eye patients were examined. All patients had moderate to severe KCS, documented by well accepted methods, and not controlled with commercially available artificial tear products, with the following findings:

8% had aqueous deficiency

26% had disturbances in two or more layers

78% had lipid deficiency

Additional research by Drs. Craig and Tomlinson of the Glasgow Caledonian University Department of Vision Sciences (Scotland) studied the left eyes of 161 normal and dry eye subjects with sensitive measurement of tear evaporation, demonstrating the following conclusion: "Where the human lipid layer is absent, or is not confluent, and the tear film is unstable, tear evaporation is increased four-fold. However, where there is a stable, intact lipid layer, regardless of lipid thickness, tear evaporation is retarded."

Despite the demonstrated importance of artificial tear formulations replicating all three layers of the normal human tear film, the vast majority of artificial tear preparations only contain certain polymers, such as one of the cellulose ethers and/or polyvinyl alcohol, in an attempt to mimic the mucin layer; along with purified water for mimicking the aqueous layer, but very few attempts have been made to incorporate a lipid component as well, and none of the latter have been a commercial success, to date. The need exists for an artificial tear formulation that replicates all three layers of the normal human tear film.

SUMMARY OF THE INVENTION

The present invention provides a composition for the effective treatment of dry eye syndrome, for contact lens rewetting, and for the ophthalmic delivery of pharmacologically active agents. This composition is formulated to replicate all three layers of the normal human tear film (mucin, aqueous, and lipid) to provide tear film stability and protection of the epithelial cells of the ocular surface. The present invention provides an aqueous artificial tear formulation having a polyvinyl alcohol, a polyvinyl acetate, a hydrophilic polymer, and a phospholipid which, in combination, replicate all three layers of the normal human tear film.

An advantage of the present invention is an artificial tear formulation for the treatment of dry eye syndrome.

Another advantage of the present invention is an artificial tear formulation that alleviates ocular surface discomfort and ocular surface damage related to dry eye syndrome.

Another advantage of the present invention is an artificial tear formulation that replicates all three layers (lipid, aqueous, mucin) of the normal human tear film.

Another advantage of the present invention is an artificial tear formulation that achieves a lengthening of tear film breakup time while also being comfortable in the eye.

Another advantage of the present invention is an artificial tear formulation that is safe, stable, and simple to manufacture.

DESCRIPTION OF THE PREFERRED EMBODIMENT

While the following description details the preferred embodiments of the present invention, it is to be understood that the invention is not limited in its application to the details of construction and arrangement of the parts illustrated in the accompanying drawings, since the invention is capable of other embodiments and of being practiced in various ways.

The present invention has a combination of polyvinyl alcohol and polyvinyl acetate as described in U.S. Pat. No. 4,744,980, which is incorporated herein by reference. Polyvinyl alcohol is manufactured by the controlled hydrolysis of polyvinyl acetate where the acetic acid is replaced by the alcoholic hydroxyl group. If at least 73% of the acetate groups is hydrolyzed the polymer is water-soluble. In the present invention, polyvinyl acetate is 73% to 93% hydrolyzed, and polyvinyl alcohol is 96% to 100% hydrolyzed. Polyvinyl alcohol with negligible acetate content is completely wettable, while polyvinyl acetate forms an adsorbed layer incompletely wettable by the solution despite its lower surface tension. By mixing the polyvinyl alcohol and the polyvinyl acetate of the present invention, it is possible to lower the surface tension of the solution while forming a completely wettable adsorbed layer over hydrophobic solids, avoiding increased viscosity which interferes with the lubricating role of the aqueous tears. In the artificial tear composition of the present invention, polyvinyl acetate ranges from about 0.5% to 10% by weight in water, preferably about 0.9%, preferably being about 87% hydrolyzed. Polyvinyl alcohol ranges from about 0.5% to 10% by weight in water, preferably about 1.8%, preferably being about 99% hydrolyzed.

The artificial tear formulation of the present invention has a hydrophilic polymer at sufficiently high concentrations to achieve an oncotic pressure of at least 45 millimeters of mercury (mmHg) without unduly increasing the viscosity of the solution. Any known hydrophilic polymer can be used but polyvinyl pyrrolidone (povidone) is preferred. The concentration of the hydrophilic polymer in the present invention is from about 0.5% to 10% by weight in water, preferably about 2%.

The artificial tear formulation also has a phospholipid ranging in concentration from about 0.003% to 0.02% by weight in water, preferably about 0.01%. Any type of phospholipid can be used, preferably a simple phospholipid, such as, for example, lecithin. A preferred source of phospholipids is Amisol® Clear manufactured by Degussa Chemical (France) which contains phospholipids (lecithin), polysorbate-80, glycerin, and ethanol. The phospholipids in Amisol® Clear range from about 3% to 20% by weight, polysorbate-80 from about 35% to 75%, glycerin from about 5% to 50%, ethanol from about 2% to 10%, and water usually at a concentration of about 10%. In a preferred embodiment of the present invention Amisol® Clear is added to the composition at a concentration of 0.02% to 0.3% by weight in water, preferably about 0.1%. Amisol® Clear also acts as a dispersing agent and prevents the formation of polymeric aggregates, which could form due to the high concentrations of the polymers in the composition. Lessening the aggregate formation in the solution increases the efficacy of the polymers. Amisol® Clear will also inhibit the formation of crystallized particles of the polymers on the eyelashes of dry eye patients. Amisol® Clear has been tested for ocular safety and toxicity in the Draize test, with satisfactory results for use in the human and animal eye.

The artificial tear formulation of the present invention also contains inorganic electrolytes that are known to contribute to the well-being of the corneal epithelium, preferably sodium chloride and potassium chloride. The inorganic electrolytes may also be selected from a group of halides and alkali divalent metals. The formulation may be preserved with any suitable preservative agent known in the art, preferably a combination of Busan-1507 (polyquaternium-42, Buckman Laboratories, Memphis, Tenn.) and disodium edetate dihydrate. The concentration of Busan-1507 is from about 0.01% to 0.0001% by weight in water, preferably about 0.001%. Busan-1507 has been tested for ocular safety and toxicity in the Draize test, with satisfactory results for use in the human and animal eye. Buffers may be added to yield a pH value between 5.0 and 8.0, such as, for example, disodium edetate dihydrate and boric acid.

An example of a preferred embodiment of the composition of the artificial tear formulation of the present invention is shown in Table 1. Values shown are percent by weight in water, preferably purified water.

TABLE 1

| Ingredient | Concentration |
| --- | --- |
| Sodium chloride | 0.560% |
| Potassium chloride | 0.080% |

TABLE 1-continued

| Ingredient | Concentration |
|---|---|
| Boric Acid | 0.200% |
| Disodium edetate dihydrate | 0.115% |
| Busan ®-1507 (60%) | 0.001% |
| Polyvinyl pyrrolidone (povidone) | 2.0% |
| Polyvinyl acetate (87% hydrolyzed) | 0.9% |
| Polyvinyl alcohol (99% hydrolyzed) | 1.8% |
| Amisol ® Clear | 0.1% |

This composition of the present invention for ophthalmic use provides an artificial tear film over the surface of an eye, producing a first layer in direct contact with the ocular surface, an aqueous layer over the first layer, and a layer of a simple phospholipid over the aqueous layer. The first layer simulates the mucin layer and is produced by the polymers (polyvinyl acetate, polyvinyl alcohol, and polyvinyl pyrrolidone). The second aqueous layer is produced by the water in the artificial tear formulation and the water in the phospholipid formulation, for example, Amisol® Clear. The lipid layer is simulated by the phospholipid in the formulation.

The composition of the present invention should be formulated so as to prevent aggregation of the polymer components and to ensure uniform mixing. A preferred method of formulating the artificial tear composition is described in Example 1.

EXAMPLE 1

A first aliquot is formed by adding to 490 milliliters of purified water sodium chloride 5.6 grams, potassium chloride 0.8 grams, boric acid 2 grams, disodium edetate dihydrate 1.15 grams, and busan-1507 0.0157 grams. These ingredients should be added to the water in the order listed above. After they have dissolved, polyvinyl pyrrolidone 20 grams is added. After it has dissolved Amisol® Clear 1 gram is added. The solution is stirred until homogeneous. The pH is adjusted to a value between 6.6 to 7.0.

A second aliquot is formed by adding to 450 milliliters of purified water polyvinyl acetate 9 grams and polyvinyl alcohol 18 grams. The solution is heated to approximately 85 degrees Celsius and stirred until complete dissolution is achieved. The pH is adjusted to a value between 6.6 to 7.0.

The first and second aliquots are mixed. Sufficient purified water is added to bring the total volume to 1 liter. The formulation may be sterilized by filtering.

The artificial tear composition of the present invention is useful and effective in the treatment of dry eye syndrome by increasing tear break up time (TBUT). Results of clinical testing of the artificial tear formulation of the present invention are shown in Example 2.

EXAMPLE 2

The effects of the artificial tear formulation of the present invention were tested in 5 patients diagnosed with dry eye syndrome having below average TBUT of 7.8±1.2 (sem) seconds (baseline). TBUT was measured by a corneal specialist ophthalmologist using standard and accepted invasive TBUT measurement techniques. The artificial tear formulation was applied topically to the eye daily as needed. After one week of daily application TBUT was 10.6+0.75 seconds, $p<0.05$ versus baseline, and after two weeks of daily application TBUT was 11.8+0.2 seconds, $p<0.05$ versus baseline. The study demonstrated that the artificial tear formulation of the present invention was safe and significantly improved TBUT in patients with dry eye syndrome. The results further suggested that the formulation improves the entire ocular surface by improving poor tear film quality.

The artificial tear formulation of the present invention may be used in the treatment of dry eye syndrome by applying this formulation topically to the conjunctiva of the eye daily as needed. The solution can be added to the conjunctiva by drops sufficient to cover the surface of the conjunctiva. The formulation can also be used to rewet contact lenses by the same method. Because the formulation contains both water and lipid, both water soluble and lipid soluble pharmacologic agents can be added to the formulation to deliver pharmacologic agents to the eye by the described method to treat various diseases and conditions of the eye.

The foregoing description has been limited to specific embodiments of this invention. It will be apparent, however, that variations and modifications may be made by those skilled in the art to the disclosed embodiments of the invention, with the attainment of some or all of its advantages and without departing from the spirit and scope of the present invention. For example, various phospholipids may be used in the formulation in addition to phospatidylcholine (lecithin) or phosphatidylethanolamine, including, for example, phosphatidylglycerols, phosphatidylinositols, diphosphatidylglycerols, phosphatidylsugars, and mixtures thereof.

It will be understood that various changes in the details, materials, and arrangements of the parts which have been described and illustrated above in order to explain the nature of this invention may be made by those skilled in the art without departing from the principle and scope of the invention as recited in the following claims.

The invention claimed is:

1. A composition for ophthalmic use, comprising:
    a) polyvinyl alcohol, wherein the concentration of said polyvinyl alcohol is from about 0.5% to 10% by weight in water, said polyvinyl alcohol being about 96% to 99% hydrolyzed;
    b) polyvinyl acetate, wherein the concentration of said polyvinyl acetate is from about 0.5% to 10% by weight in water, said polyvinyl acetate being about 73% to 93% hydrolyzed;
    c) polyvinyl pyrrolidone, wherein the concentration of said polyvinyl pyrrolidone is from about 0.5% to 10% by weight in water; and
    d) a phospholipid, wherein the concentration of said phospholipid is from about 0.003% to 0.02% by weight in water.

2. The composition of claim 1 wherein said phospholipid is formulated in polysorbate-80, glycerin, ethanol, and water.

3. The composition of claim 1 wherein said phospholipid is lecithin.

4. The composition of claim 1 further comprising water, one or more electrolytes to contribute to the well being of the corneal epithelium, one or more preservatives, and one or more buffers.

* * * * *